(12) United States Patent
Chukinas (10) Patent No.: US 11,395,688 B2
(45) Date of Patent: Jul. 26, 2022

(54) TOOL FOR CRIMPING ORTHOPEDIC CABLE

(71) Applicant: DEPUY SYNTHES PRODUCTS, INC., Raynham, MA (US)

(72) Inventor: Jonathan James Chukinas, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 505 days.

(21) Appl. No.: 16/588,327

(22) Filed: Sep. 30, 2019

(65) Prior Publication Data
US 2021/0093367 A1    Apr. 1, 2021

(51) Int. Cl.
| A61B 17/58 | (2006.01) |
| A61B 17/60 | (2006.01) |
| A61F 2/00 | (2006.01) |
| A61B 17/88 | (2006.01) |
| A61B 17/00 | (2006.01) |

(52) U.S. Cl.
CPC ...... *A61B 17/8861* (2013.01); *A61B 17/8863* (2013.01); *A61B 2017/00407* (2013.01); *A61B 2017/00424* (2013.01); *A61B 2017/00477* (2013.01)

(58) Field of Classification Search
CPC combination set(s) only.
See application file for complete search history.

(56) References Cited

U.S. PATENT DOCUMENTS

| 5,199,146 A | 4/1993 | Grover |
| 5,395,374 A | 3/1995 | Miller et al. |
| 5,788,697 A | 8/1998 | Kilpela et al. |
| 5,902,305 A | 5/1999 | Beger et al. |
| 5,935,130 A | 8/1999 | Kilpela et al. |
| 6,077,268 A | 6/2000 | Farris et al. |
| 6,364,885 B1 | 4/2002 | Kilpela et al. |
| 6,544,267 B1 | 4/2003 | Cole et al. |
| 6,565,944 B1 | 5/2003 | Hartness et al. |
| 6,761,722 B2 | 7/2004 | Cole et al. |
| 7,704,252 B2 | 4/2010 | Albertson et al. |

(Continued)

OTHER PUBLICATIONS

Written Opinion of the International Searching Authority re PCT/IB2020/O58016 dated Dec. 7, 2020; 7 pgs.

(Continued)

*Primary Examiner* — Sameh R Boles
(74) *Attorney, Agent, or Firm* — Kramer & Amado, P.C.

(57) ABSTRACT

A crimping tool for crimping a crimp onto a cable includes a crimping unit, a housing unit, and a tensioning unit. The crimping unit includes an inner crimping tube having a distal end configured to receive the cable; and an outer crimping tube mounted around the inner crimping tube. The housing unit is configured to receive the outer crimping tube, and includes a housing having an open lower portion; a trigger-handle; and a first hinge connecting the trigger-handle to the housing. The tensioning unit is mounted to the housing, and is configured to apply tension to the cable. The trigger-handle releasably engages the open lower portion of the housing by rotation about the first hinge; and the outer crimping tube is configured to move in an axial direction relative to the inner crimping tube to crimp the cable when actuated by the trigger-handle.

16 Claims, 11 Drawing Sheets

(56) References Cited

U.S. PATENT DOCUMENTS

| | | |
|---|---|---|
| 8,096,998 B2 | 1/2012 | Cresina |
| 8,257,367 B2 | 9/2012 | Bryant et al. |
| 8,419,736 B2 | 4/2013 | Albertson et al. |
| 8,469,966 B2 | 6/2013 | Allen et al. |
| 8,617,185 B2 | 12/2013 | Bonutti et al. |
| 8,992,543 B2 | 3/2015 | Yamaguchi et al. |
| 9,055,984 B2 | 6/2015 | Albertson et al. |
| 9,216,047 B2 | 12/2015 | Bryant et al. |
| 9,295,507 B2 | 3/2016 | Albertson et al. |
| 9,402,668 B2 | 8/2016 | Bonutti et al. |
| 9,956,021 B1 * | 5/2018 | Aebi .................. A61B 17/8863 |
| 2008/0195145 A1 | 8/2008 | Bonutti et al. |
| 2017/0049487 A1 | 2/2017 | Bonutti et al. |
| 2017/0340374 A1 | 11/2017 | Xie |

OTHER PUBLICATIONS

International Search Report dated Nov. 25, 2020 re PCT/IB2020/058016; 5 pgs.

\* cited by examiner

TOOL FOR CRIMPING ORTHOPEDIC CABLE

TECHNICAL FIELD

This disclosure relates generally to an apparatus for crimping a crimp onto a cable.

BACKGROUND

During certain surgical procedures, specifically during orthopedic surgical procedures, it is a common requirement to anchor two or more elements together, such as pieces of a bone, two or more bones, or a combination of soft tissue and bone. This has been accomplished by a number of devices, such as bone bolts that penetrate two pieces of bone and use a nut to draw the segments together, bone screws and interconnecting plates, wires circling at least two pieces of bone, or sutures into the tissue.

Often such devices require a relatively large access opening through surrounding and/or covering tissue to implant and operate the anchoring devices. The enlarged access opening may increase patient pain and lengthen recovery time for the patient. Further, in some operation locations, it is difficult and impractical to make these large access openings to reach the appropriate site because of surrounding joints and blood vessels.

Cerclage systems provide an alternative to implants that must penetrate the bone to achieve fixation. These systems rely on passing a cable around two segments of bone and then tensioning, crimping and cutting the cable to squeeze the bone segments together. A significant drawback of these systems is that they require access around the entire bone.

SUMMARY OF EXEMPLARY EMBODIMENTS

A brief summary of various embodiments is presented below. Embodiments address the need to crimp a crimp onto an orthopedic cable. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments disclosed herein relate to a crimping tool for crimping a crimp onto a cable, including a crimping unit, a housing unit, and a tensioning unit. In various embodiments, the crimping tool includes:
  a) a crimping unit, including an inner crimping tube having a distal end configured to receive the cable; and an outer crimping tube mounted around the inner crimping tube.
  b) a housing unit, including a housing having a barrel with an open lower portion and an open distal end configured to receive the outer crimping tube of the crimping unit; a trigger-handle including an upper handle portion configured to engage the open lower portion of the barrel of the housing, a palmrest mounted to the upper handle portion, and a trigger rotatably mounted to the upper handle portion; and a first hinge connecting the trigger-handle to the housing; and
  c) a tensioning unit mounted to a proximal end of the barrel on the housing, where the tensioning unit is configured to apply tension to a cable passing through the inner crimping tube and the barrel of the housing.

In various embodiments, the trigger-handle is configured to releasably engage the open lower portion of the housing by rotation about the first hinge; and the outer crimping tube is configured to move in an axial direction relative to the inner crimping tube to crimp the cable when actuated by the trigger-handle.

In various embodiments, the trigger-handle of the crimping tool is configured to releasably engage the open lower portion of the housing so as to hold the outer crimping tube between the housing and the trigger-handle. A groove on the outer crimping tube may be provided, where the groove engages a pin on the trigger handle. The pin may be configured to move the outer crimping tube over the distal end of the inner crimping tube when the trigger-handle is actuated. In various embodiments, the distal end of the inner crimping tube is configured to radially contract when the outer crimping tube moves thereover.

In various embodiments, the housing unit includes a housing having an open lower portion; a trigger-handle; a hinge connecting the trigger-handle to the housing; and a latching mechanism configured to releasably engage a pin on the housing.

In various embodiments, crimping may be uniaxial without radial deflection of the cable.

In various embodiments, a groove on the outer crimping tube may be configured to engage a pin on the trigger handle of the crimping tool, and a proximal end of the inner crimping tube may be configured to engage a stopping surface in the housing. In various embodiments, the crimping unit may consist of an inner crimping tube and an outer crimping tube, where the inner crimping tube is made from a single part and the outer crimping tube is made from a single part.

In various embodiments of the crimping tool, the trigger-handle includes an upper handle portion configured to engage the open lower portion of the housing by rotation about the first hinge; a palmrest connected with the upper handle portion; and a trigger connected to the upper handle portion by a second hinge. In various embodiments, the trigger is configured to rotate about the second hinge in a single direction from a start position until a defined angular rotation has been achieved; and return to the start position after the defined angular rotation has been achieved.

In various embodiments of the crimping tool, the trigger-handle includes an upper handle portion configured to engage the open lower portion of the housing by rotation about the first hinge; a palmrest connected with the upper handle portion; a trigger connected to the upper handle portion by a second hinge; a ratchet having a plurality of teeth connected with the upper handle portion; and a pawl connected with the trigger. The pawl may have a first surface and a second surface, where the first surface of the pawl is configured to engage the plurality of teeth on the ratchet so as to allow rotation of the trigger about the second hinge in a single direction. In various embodiments, the second surface of the pawl does not engage the plurality of teeth on the ratchet, allowing rotation of the trigger about the second hinge in a second direction opposite to the single direction.

In various embodiments of the crimping tool, the trigger-handle includes an upper handle portion configured to engage the open lower portion of the housing by rotation about the first hinge; an ergonomically designed palmrest connected with the upper handle portion; and a trigger connected to the upper handle portion by a second hinge. The ergonomically designed palmrest may include a rear surface configured to engage the palm of a user, and a horn spaced from the housing; where the horn is configured to engage the user's hand between a thumb and a forefinger.

In various embodiments of the crimping tool, the trigger-handle includes an ergonomically designed trigger, which may have an arc-shaped outer surface configured to engage the user's fingers.

Various embodiments disclosed herein relate to a crimping tool including a housing unit configured to receive an outer crimping tube and an inner crimping tube positioned in the outer crimping tube. In various embodiments, the housing unit may include a housing having an open lower portion; a trigger-handle; and a first hinge connecting the trigger-handle to the housing. A tensioning unit may be mounted to the housing, where the tensioning unit is configured to apply tension to a cable in the inner crimping tube. The trigger-handle may be configured to releasably engage the open lower portion of the housing by rotation about the first hinge; and to drive the outer crimping tube in a distal direction relative to the inner crimping tube to crimp the cable.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

These and other more detailed and specific features of the invention are more fully disclosed in the following specification, reference being had to the accompanying drawings, in which.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION OF EMBODIMENTS OF THE INVENTION

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. Descriptors such as "first," "second," "third," etc., are not meant to limit the order of elements discussed, are used to distinguish one element from the next, and are generally interchangeable.

The crimping tool provides a convenient and effective system for securing two segments of bone together while operating on a single axis. Such a system may be operable through a relatively small insertion opening or openings to securely hold two bone segments together.

The crimping tool is a pistol shaped, two-hand operable tensioning and crimping device which functions to crimp a cable. The crimping tool is a multi-use tool which is capable of crimping a crimp onto a cable of up to 2.0 millimeter in diameter, e.g., from 0.2 mm to 2 mm, from 0.5 mm to 1.5 mm, or from 0.8 mm to 1.2 mm.

Embodiments of the crimping tool are described below, including the three components of the tensioning and crimping tool which include a crimping unit 1 including an inner crimping tube 4 positioned within an outer crimping tube 5; a housing unit 2 configured to receive the outer crimping tube 5 of the crimping unit 1; and a tensioning unit 3.

Figure 1:
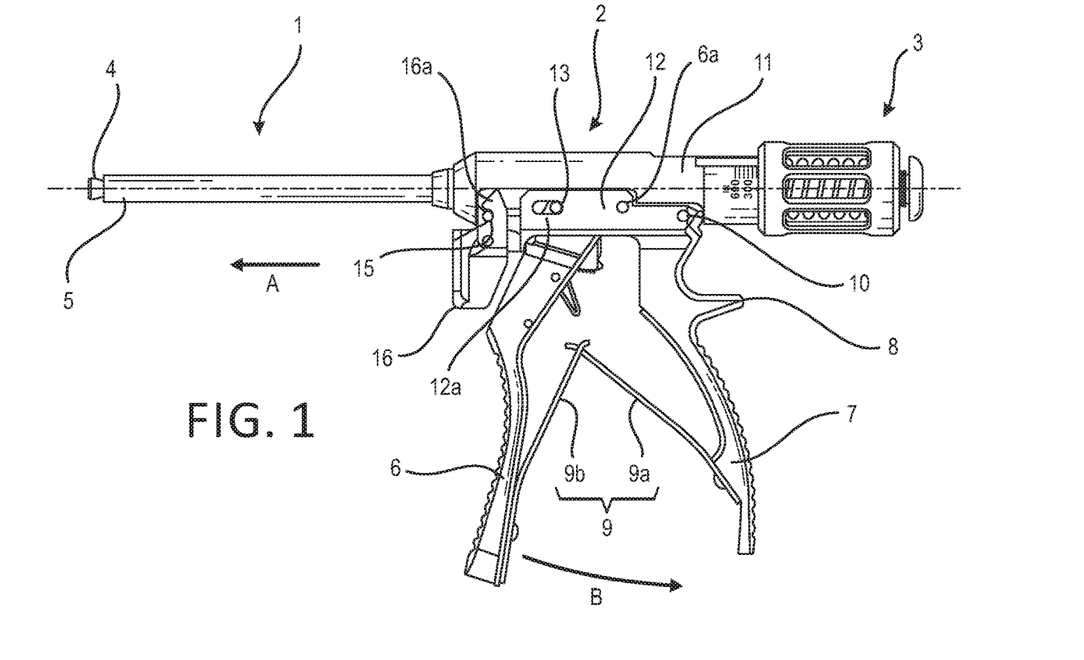
FIG. 1 is a side view of the crimping tool, prior to crimping.

FIG. 1 shows the crimping tool, which includes crimping unit 1 and housing unit 2. The crimping unit 1 includes an inner crimping tube 4 having a distal end configured to receive the cable; and an outer crimping tube 5 mounted around the inner crimping tube 4, so that only the distal end of tube 4 is exposed. The housing unit 2 is configured to receive the outer crimping tube 5 of the crimping unit, with inner crimping tube 4 being positioned within the outer crimping tube. Housing unit 2 includes a housing 11 having a barrel with an open lower portion; a trigger-handle; and a first hinge connecting the trigger-handle to the housing. The trigger-handle is configured to releasably engage the open lower portion of the housing by rotation about the first hinge; and the outer crimping tube is configured to move in an axial direction relative to the inner crimping tube to crimp the cable when actuated by the trigger-handle.

Figure 2:
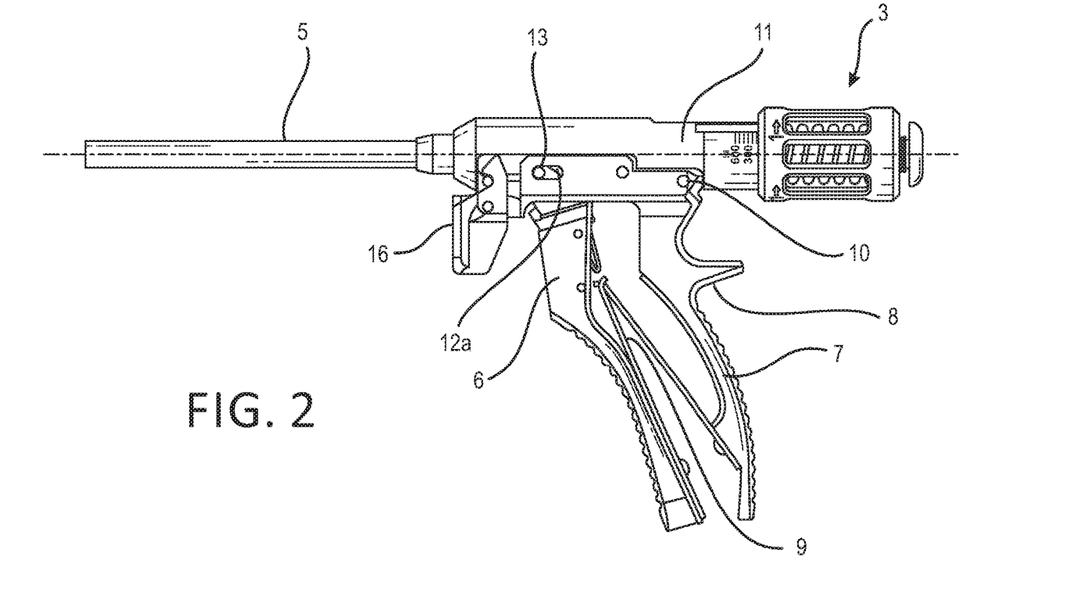
FIG. 2 is a side view of the crimping tool, after crimping.

As seen in FIG. 1, the trigger handle includes an upper handle portion 12 which engages the open lower portion of housing 11, a palmrest 7 with a horn 8 which may be rigidly connected with the upper handle portion, and a trigger 6 which is connected to upper handle portion 12 by a hinge or a rotating joint, where the hinge or rotating joint rotates about pin 6a. Trigger 6 and palmrest 7 are biased away from each other by leaf spring 9, which may be a single spring or two intersecting springs 9a and 9b. When the trigger 6 is pulled in the direction of arrow B toward palmrest 7, the trigger 6 rotates around a hinge or a rotating joint anchored to pin 6a. A pin 13 carried by trigger 6 moves in slot 12a of the upper handle portion in a distal direction as trigger 6 rotates. Pin 13 engages the outer surface of outer crimping tube 5, which is positioned between upper handle portion 12 and housing 11, and drives outer crimping tube 5 distally in the direction of arrow A as trigger 6 rotates. When trigger 6 is fully depressed, as shown in FIG. 2, pin 13 has moved from a proximal position in slot 12a to a distal position, causing outer crimping tube 5 to completely cover the inner crimping tube. As seen in FIG. 1, the upper handle portion 12 is connected to housing 11 by hinge 10 and a latch 16 with a hook 16a which engages pin 15.

Figure 3:
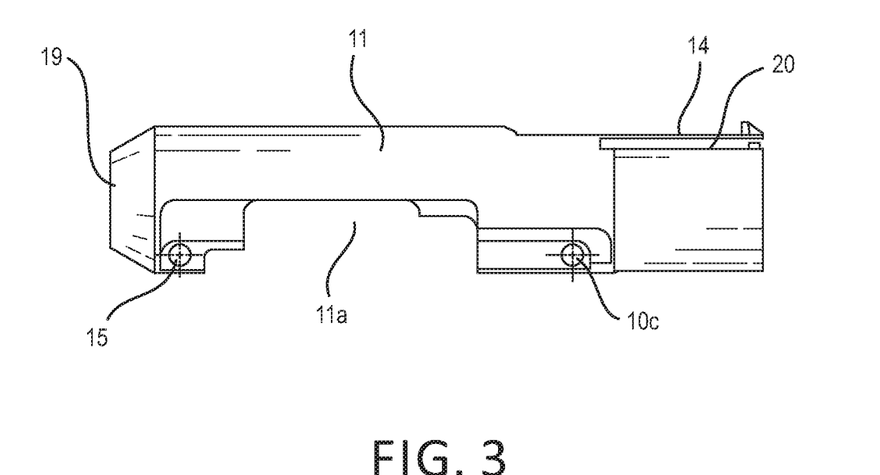
FIG. 3 shows the housing of the crimping tool of FIG. 1.

FIG. 3 shows housing 11. Housing 11 has a generally cylindrical barrel (but may be other shapes as well), with an open end 19 configured to receive outer crimping tube 5 of FIG. 1. Open lower portion 11a of housing 11 is configured to engage upper handle portion 12 of FIG. 1. The housing has a pin 15 configured to engage latch 16 of FIG. 1. Leaf clip 14 of housing 11 is mounted at the proximal end of housing 11, above a generally planar surface 20. In FIG. 3, hole 10c is configured to receive a pin for use in forming hinge 10 of FIG. 1.

Figure 4:
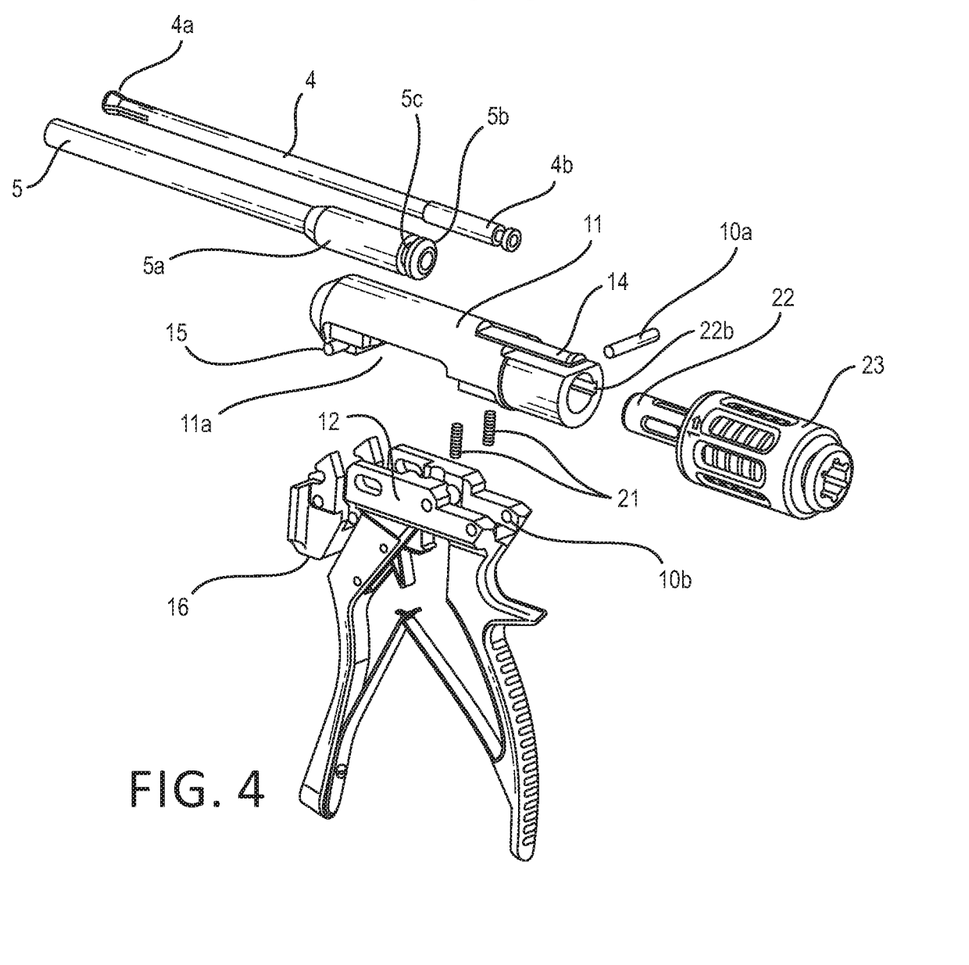
FIG. 4 shows an exploded view of the crimping tool of FIG. 1.

FIG. 4 shows an exploded view of the apparatus of FIG. 1. Inner crimping tube 4 has an expanded distal head 4a having longitudinal slits therein, and an enlarged proximal end 4b. Outer crimping tube 5 has an enlarged proximal end 5a. In use, outer crimping tube 5 is positioned over crimping tube 4 so that the enlarged proximal end 4b of tube 4 is engaged by the enlarged proximal end 5b of outer tube 5, while leaving the expanded distal head 4a exposed at the distal end of tube 5. Outer crimping tube 5 has a flange 5b at the proximal end of tube 5, with a circumferential notch 5c between flange 5b and enlarged proximal end 5a. The assembly of crimping tubes 4 and 5 is inserted into housing 11, with the enlarged proximal end 5a entering an open end 19 of housing 11. Housing 11 has a lower open portion 11a and pins 15. The upper handle portion 12 of the trigger handle is configured to releasably mate with the open lower portion 11a of housing 11. The upper handle portion 12 is connected with housing 11 so that upper handle portion 12 covers the open lower portion 11a of housing 11, and is connected to housing 11 by a hinge, formed by pin 10a, which passes through holes 10b on upper handle portion 12 and hole 10c on housing 11, shown in FIG. 3, and by a latch 16 rotatably mounted to upper handle portion 12, where latch 16 releasably engages pins 15. Compression springs 21 may bias the upper surface of upper handle portion 12 away from housing 11 when latch 16 is disengaged from pins 15.

Figure 18:
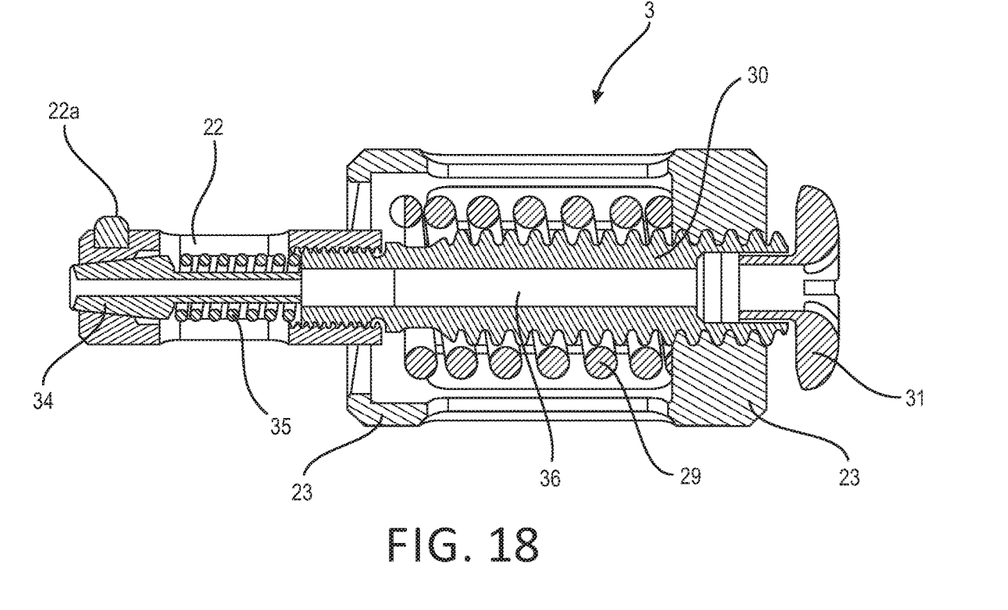
FIG. 18 is a cross sectional side view of the tensioning unit.

As shown in FIG. 4, the crimping tool may also include a tensioning unit 3, including a cone sheath 22 which is insertable into an end of housing 11, and a rotatable tensioning nut 23 which is adapted to receive the proximal end of housing 11 until leaf clip 14 engages a lip (not shown) inside nut 23. Rotation of cone sheath 22 relative to housing 11 is prevented by engagement between a slot 22b in housing 11 and a guiding cam 22a on cone sheath 22, where guiding cam 22a is shown in FIG. 18. The tensioning unit is described in further detail herein, as well as in U.S. Pat. No. 9,956,021, incorporated herein by reference.

Figure 5:
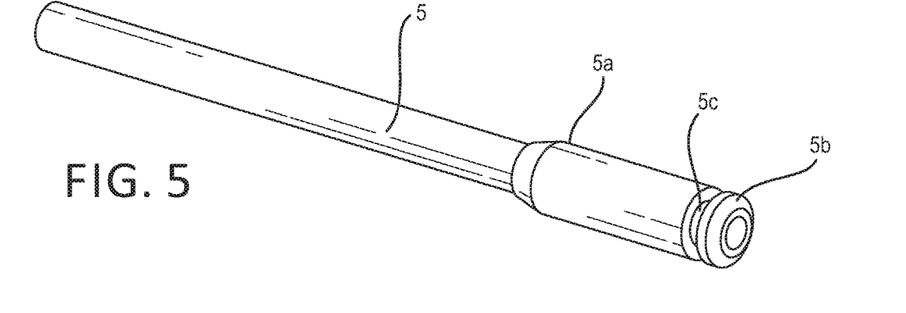
FIG. 5 illustrates a side view of the outer crimping tube

FIG. 5 shows the outer crimping tube 5. Tube 5 has a proximal end configured to slide into an open end 19 of housing 11, as shown in FIG. 4. The tube 5 has an enlarged proximal end 5a which has a diameter configured to fit within housing 11. A flange 5b is adjacent to the enlarged end 5a, with a cylindrical notch 5c between the enlarged end 5a and the flange. The enlarged end 5a and the flange 5b have similar diameters, and hold the tube 5 in housing 11 of FIG. 4 so that the tube and the housing are coaxial. Tube 5 may be formed from a single metal part.

Figures 6, 7, 8:
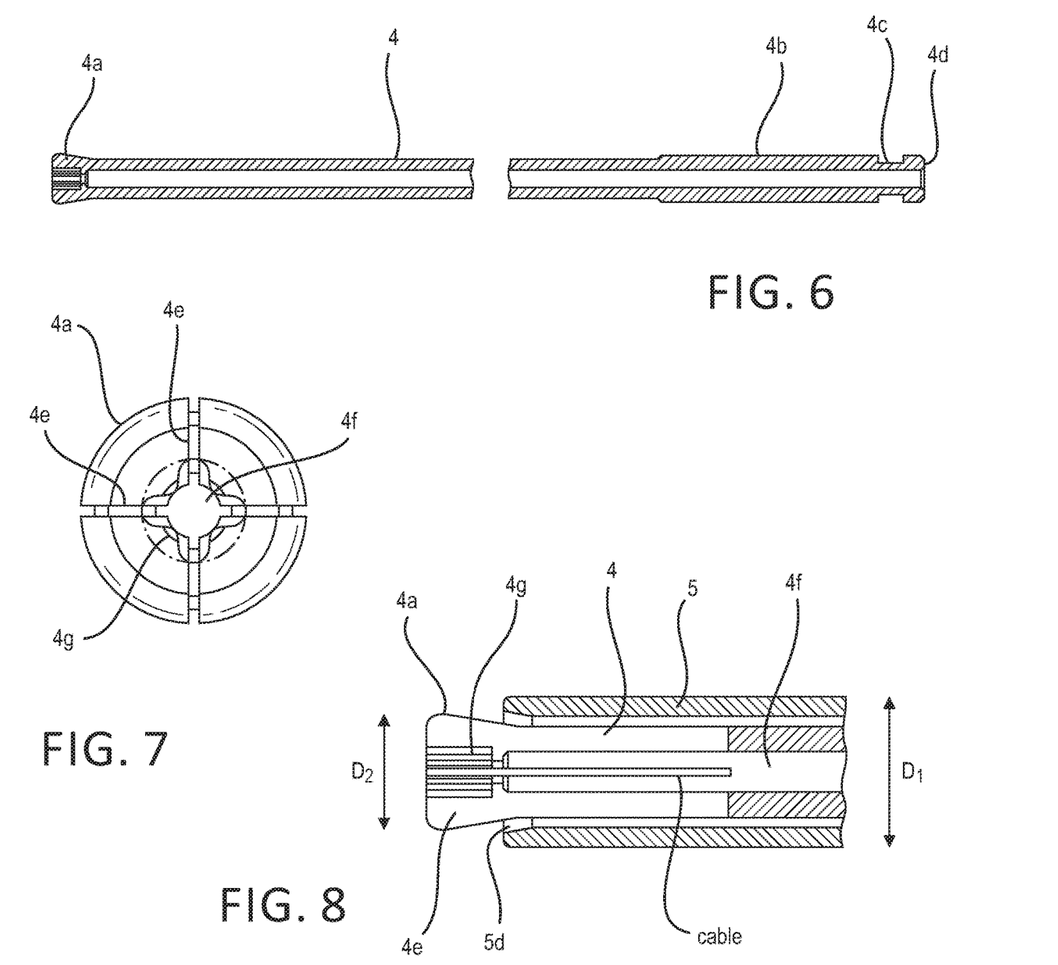
FIG. 6 illustrates a cross sectional view of the inner crimping tube.
FIG. 7 illustrates a view of the distal end of the inner crimping tube.
FIG. 8 illustrates a cross sectional view of the distal end of the inner crimping tube within the outer crimping tube.

FIG. 6 shows the inner crimping tube 4. Tube 4 has a proximal end configured to slide into the an opening 5d of the distal end of tube 5, as shown in FIG. 8. The tube 4 has an enlarged proximal end 4b which has a diameter configured to fit within tube 5, so that tubes 4 and 5 are coaxial and a conical distal end 4a. A cylindrical notch 4c may be present between the enlarged end 4b and the end of the tube 4. The tube 4 may have a proximal end surface 4d. Tube 4 may be formed from a single metal part.

FIG. 7 shows an end view of the conical distal end 4a of tube 4. Tube 4 has a bore 4f configured to receive a cable along an axis of tube 4. Within the conical end 4a, the inner surface of hole 4f may have scallops 4g. Slits 4e are present in conical distal end 4a of tube 4.

FIG. 8 shows the inner crimping tube 4 positioned in the outer crimping tube 5 so that the conical distal end 4a of tube 4 is exposed. The inner diameter D1 of tube 5 is less than the maximum outer diameter D2 of conical distal end 4a. A cable is positioned within the bore 4f of tube 4. When outer crimping tube 5 is moved in a distal direction over conical end 4a in the direction of arrow D, the inner surface of tube 5 compresses the conical end 4a of tube 4. During compression, the maximum radius of conical portion 4a is reduced as adjacent edges of slits 4e are forced together by radial forces exerted on the outer surface of conical portion 4a by the inner surface of tube 5. Scallops 4g on the inner surface of bore 4f then are driven radially inward toward the cable, and crimp a metal crimp onto the cable. In various embodiments, scallops 4g are evenly disposed about the inner surface of tube 4, and crimp the cable uniaxially, without introducing any radial deflection into the cable or bending the cable.

Figure 9:
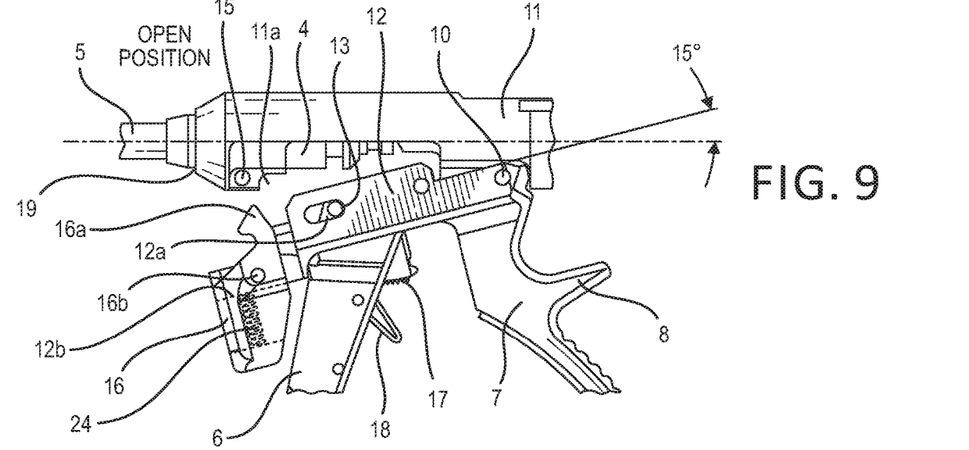
FIG. 9 is a side view of the crimping tool of FIG. 1, with the trigger-handle assembly in a fully open position.

FIG. 9 shows the upper handle portion 12 and the housing 11 in an open position, with the outer crimping tube 5 being positioned in the open end 19 of housing 11. Hook 16a of latch 16 is disengaged from pin 15, and upper handle portion 12 rotates about hinge 10 by about 15 degrees, relative to housing 11. Compression springs 21, shown in FIG. 4, may be mounted between upper handle portion 12 and housing 11, and may aid in pushing upper handle portion 12 away from housing 11 when latch 16 is disengaged. The lower surface of the proximal end of outer crimping tube 4 is visible through the opening 11a in housing 11. Compression spring 24 is mounted between latch 16 and a lower surface 12b of upper handle portion 12, and biases latch 16 to rotate into an initial start position about hinge 16b.

Figure 10:
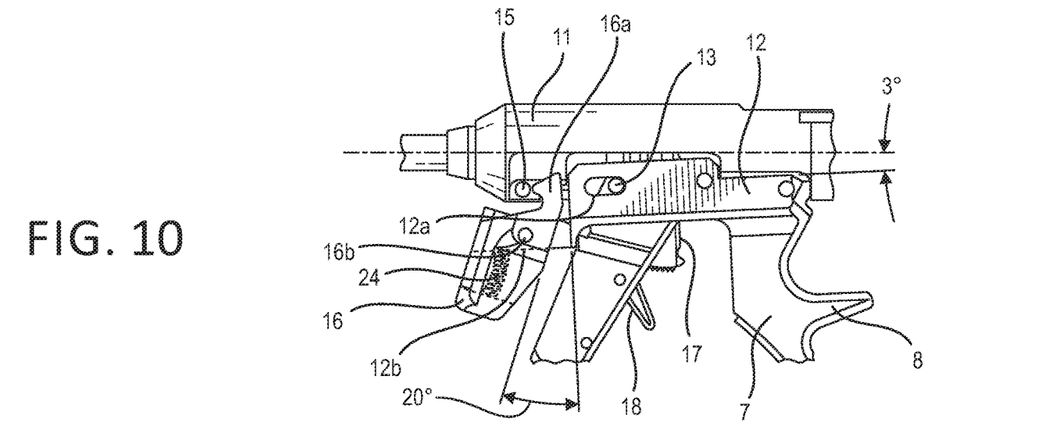
FIG. 10 is a side view of the crimping tool of FIG. 1, with the trigger-handle assembly in a partially open position.
Figure 11:
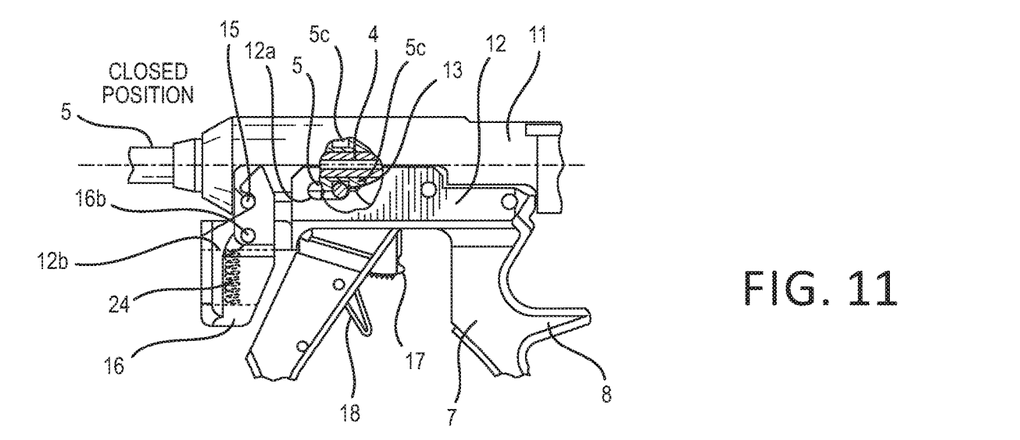
FIG. 11 is a side view of the crimping tool of FIG. 1, with the trigger-handle assembly in a closed position.

FIG. 10 shows the housing 11 and the upper handle portion 12 in a partially open position. Latch 16 is rotated by about 20 degrees about hinge 16b, while hook 16a contacts pin 15 without engaging pin 15. In this position, rotation of latch 16 about hinge 16b compresses spring 24 between latch 16 and upper handle portion 12. Compression on spring 24 may be released by rotating upper handle portion 12 about hinge 10 until it contacts housing portion 11, allowing latch 16 to engage pin 15 as shown in FIG. 11. Alternatively, compression on spring 24 may be released by rotating upper handle portion 12 about hinge 10 away from housing portion 11, allowing latch 16 to fully disengage pin 15 as shown in FIG. 9.

FIG. 11 shows the housing 11 and the upper handle portion 12 in a closed position. Outer crimping tube 5 is positioned in open end 19 of housing 11. A proximal end of housing 11 is connected to upper handle portion 12 by hinge 10. A distal end of housing 11 is connected to upper handle portion 12 by latch 16, which engages pin 15. A compression spring 24 mounted between upper handle portion 12 and latch 16 biases latch into a position in which hook 16a on latch 16 engages pin 15. The cutaway portion of FIG. 5 shows the proximal end of outer crimping tube 5, as well as inner crimping tube 4 within tube 5. As seen in FIG. 5, when the handle is latched to the housing 11, pin 13, slidably engaged by slot 12a, is positioned between tube 5 and flange 5b on tube 5, in notch 5c. Thus, the outer crimping tube cannot move independently of pin 13 when latch 16 engages pin 15. Also, if a user attempts to engage latch 16 and pin 15 to close housing 11 and upper handle portion 12 about hinge 10, latch 16 will not close unless notch 5c and pin 13 are properly aligned. Rotation of latch 16 about hinge 16b compresses spring 24 against upper handle portion 12 and disengages latch 16 from pin 15, allowing the upper handle portion 12 and the housing 11 to be opened by rotation about hinge 10.

Figure 12:
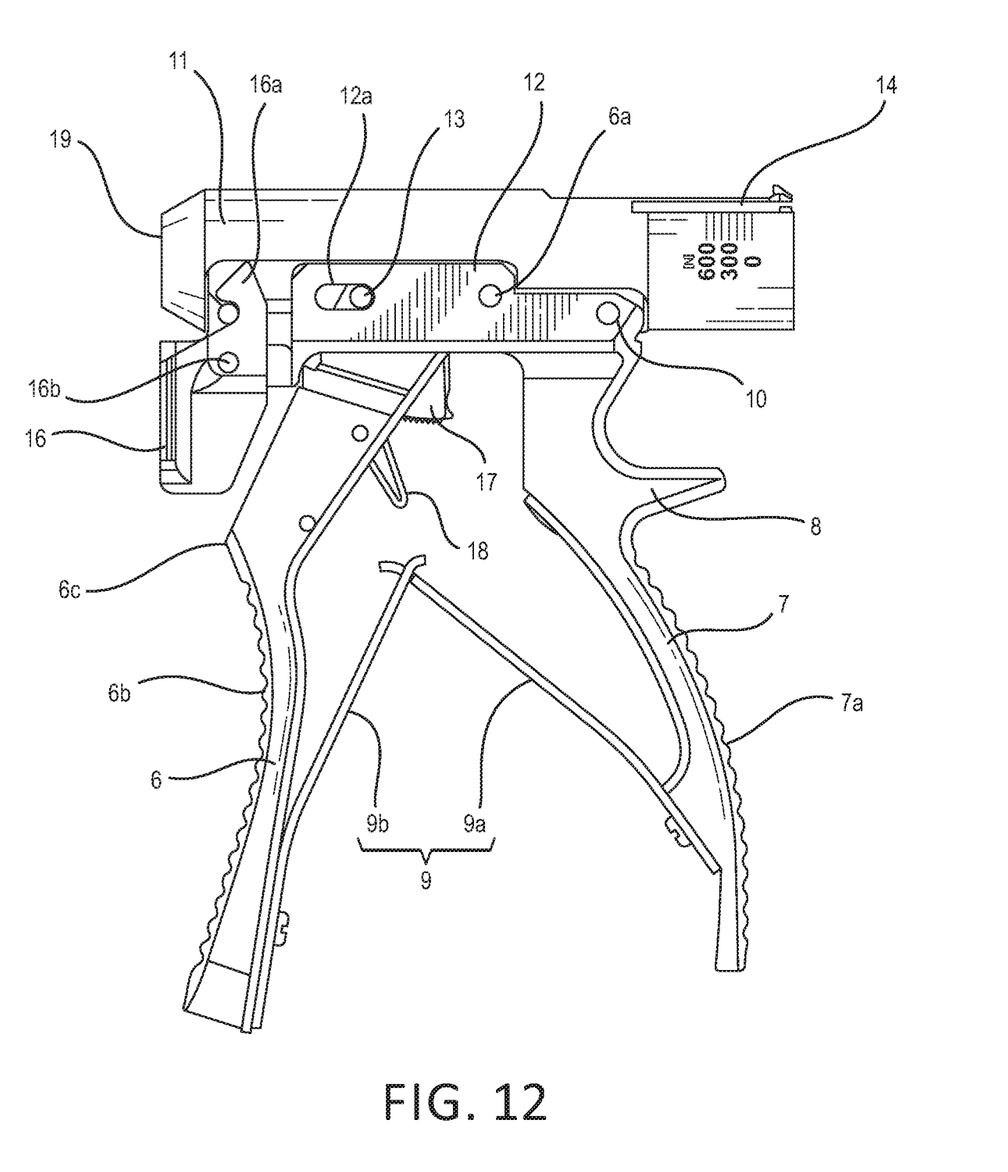
FIG. 12 is a side view of the trigger-handle unit of the crimping tool of FIG. 1.

FIG. 12 shows a view of the crimper of FIG. 1, prior to insertion of crimping unit 1 or tensioning unit 3. Housing 11 includes an open distal end 19, configured to receive the enlarged proximal end 5a of the outer crimping tube 5, as shown in FIG. 5. The lower portion of housing 11 has a shape which is configured to engage the upper handle portion 12 of the trigger handle. The upper handle portion 12 is connected with housing 11 so that upper handle portion 12 is connected to housing 11 by hinge 10, and by a latch 16 which is rotatable about a hinge 16b and has a hook 16a. As shown in FIG. 12, hook 16a on latch 16 releasably engages pin 15. Movement of trigger 6 toward palmrest 7 about a hinge or rotating joint connected with pin 6a is controlled by a ratchet 17 and a pawl 18. As seen in FIG. 12, the palmrest 7 may have a surface 7a with a convex shape configured to fit comfortably in a user's hand, and a horn 8 configured to fit between the user's thumb and forefinger. The trigger 6 may have a surface 6b with a concave surface designed to be gripped by a user's fingers. In use, horn 8 prevents the user's palm from moving upwards toward housing 11. The upper end 6c of concave surface 6b prevents the user's fingers from moving upwards toward housing 11. The gripping surfaces of palmrest 7 and trigger 6 are therefore ergonomically designed to maintain a comfortable distance between the user's hand and housing 11. This helps maintain leverage as trigger 6 is squeezed toward palmrest 7 against spring 9. In the absence of horn 8 and concave surface 6b, the user's hand might slide toward housing 11, reducing leverage when squeezing the trigger against the palmrest.

Figure 13:
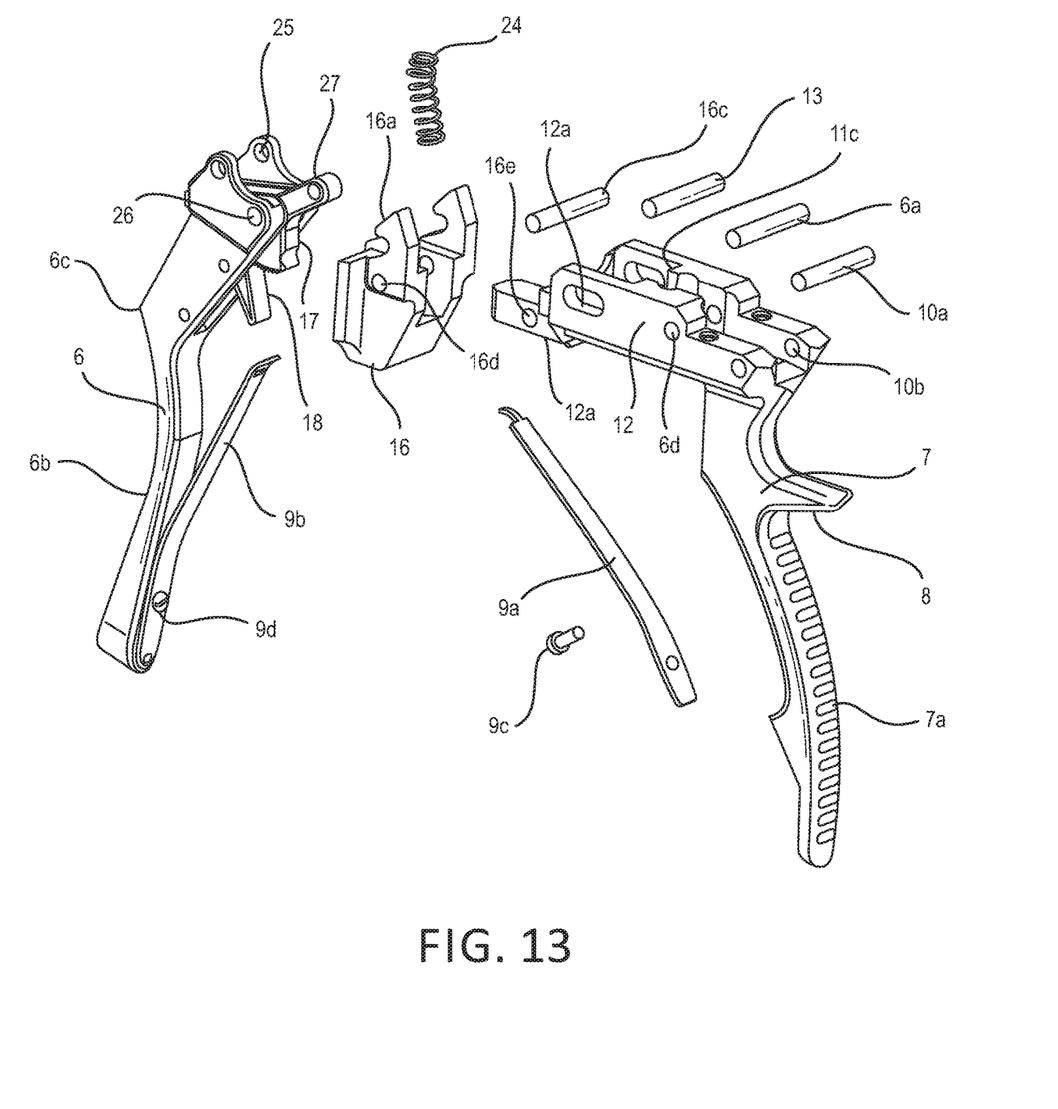
FIG. 13 is an exploded view of the trigger-handle unit of the crimping tool of FIG. 1.

FIG. 13 shows an exploded view of the trigger-handle assembly for use in the housing unit 2 of FIG. 1. The trigger-handle assembly includes trigger 6, spring 9b anchored to handle 6 by screw or bolt 9d, ratchet 17, and pawl 18. The ratchet rotates about hinge 26.

The handle includes a palmrest 7 fixed to upper handle portion 12, where handle portion 12 has a lower surface 12b. The handle includes a spring 9a fixed to palmrest 7 by screw or nut 9c. A prong on the free end of spring 9a is received by a hole in the free end of spring 9b. Alternatively, a single leaf spring may extend from palmrest 7 to trigger 6.

Ratchet 17 includes a free end 27 with a hole therethrough. The hole on free end 27 is rotatably anchored to upper handle portion 12 by pin 6a, which passes through holes 6d on upper handle portion 12. Holes 25 on the trigger handle 6 are rotatably mounted on pin 13, which is slidably engaged by slot 12a on upper handle portion 12. Pins 6a and 13 thus hold trigger handle 6 and upper handle portion 12 together.

Latch 16 has holes 16d, which are rotatably mounted on pin 16c which passes through holes 16e in upper handle portion 12. Pin 16c, together with holes 16d and 16e, form hinge 16b, shown in FIGS. 9-11. Spring 24 is mounted between latch 16 and lower surface 12b of upper handle portion 12.

Pin 10a forms hinge 10 between upper handle portion 12 and housing 11, as seen in FIGS. 9-11. Pin 10a passes through hole 10c in housing 11, shown in FIG. 3, and holes 10b in upper handle portion 12, allowing upper handle portion 12 to rotate relative to housing 11.

Figures 14, 15:
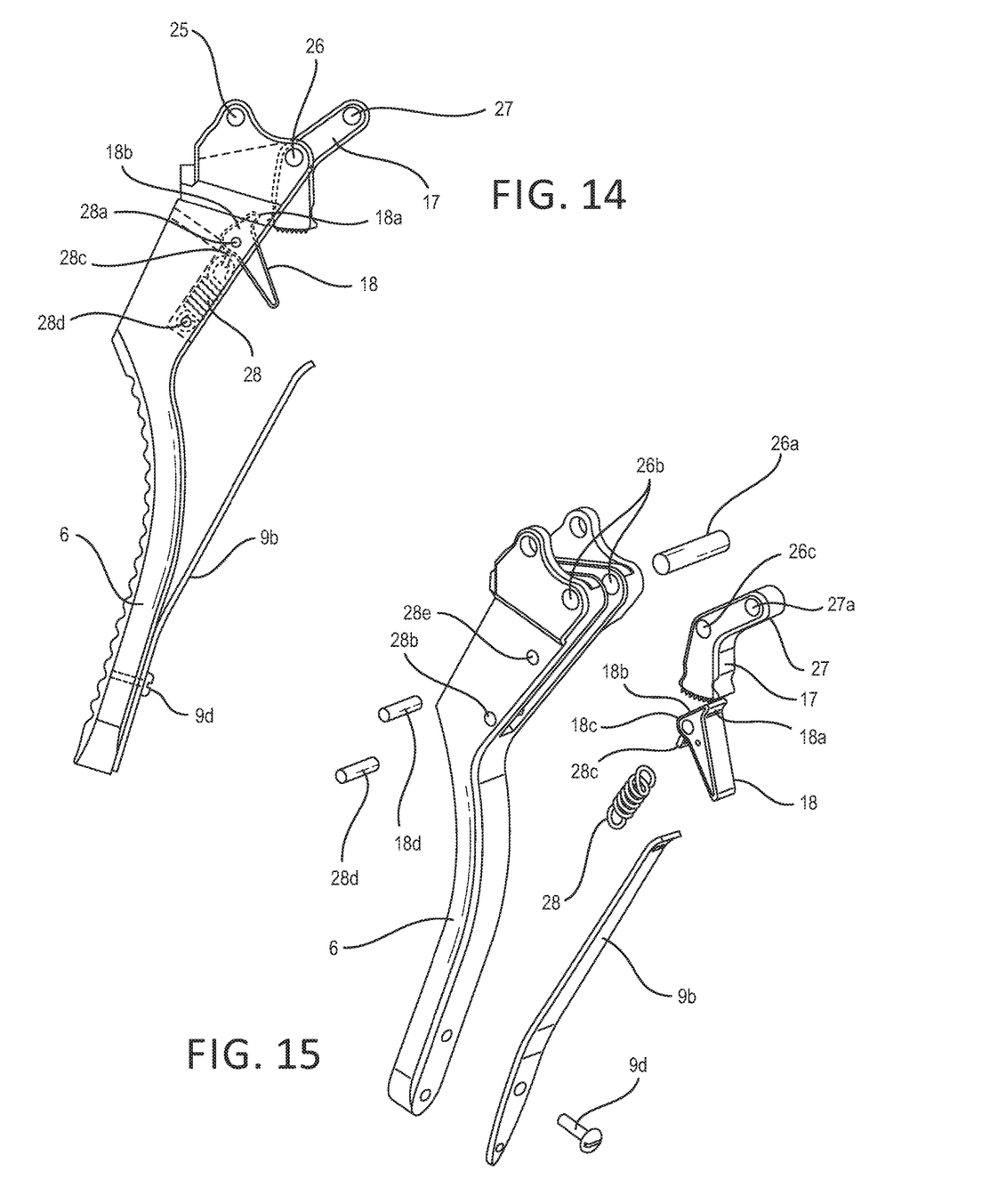
FIG. 14 is a view of the trigger of the crimping tool of FIG. 1.
FIG. 15 is an exploded view of the trigger of the crimping tool of FIG. 1.

The positioning of ratchet 17 and pawl 18 in trigger 6 are shown in FIG. 14. Ratchet 17 rotates about hinge 26. Pawl 18 rotates on hinge 28a, and is configured to move past a toothed surface of ratchet 17 in either a forward direction, toward palmrest 7, or a reverse direction. Pawl 18 has a tooth 18a configured to engage any pair of adjacent teeth on ratchet 17 as the pawl moves in a forward direction. When tooth 18a engages a pair of adjacent teeth on ratchet 17, tooth 18a is able to move past the adjacent teeth on the ratchet in only a single direction, the forward direction. The pawl also has a planar surface 18b configured to contact the teeth of the ratchet 17 as the pawl moves in a reverse direction. Planar surface 18b does not engage adjacent teeth on the ratchet, allowing planar surface 18b to move in the reverse direction over the toothed surface of the ratchet. A spring 28 mounted between pin 28d and pawl 18 biases pawl 18 into a first position in which tooth 18a is configured to engage the teeth of ratchet 17.

FIG. 15 shows an exploded view of the ratchet and pawl assembly of FIG. 14. The ratchet 17 is connected to the trigger 6 by pin 26a, which engages holes 26b on the trigger and hole 26c on the ratchet, forming hinge 26 as shown in FIG. 14. Pawl 18 is rotatably connected to trigger 6 by pin 18d, which passes through hole 18c on pawl 18 and holes 28e on trigger 6, forming hinge 28a as shown in FIG. 14. Spring 28 is connected between hook 28c on pawl 18 and pin 28d, which passes through holes 28b on trigger 6.

Figure 16A:
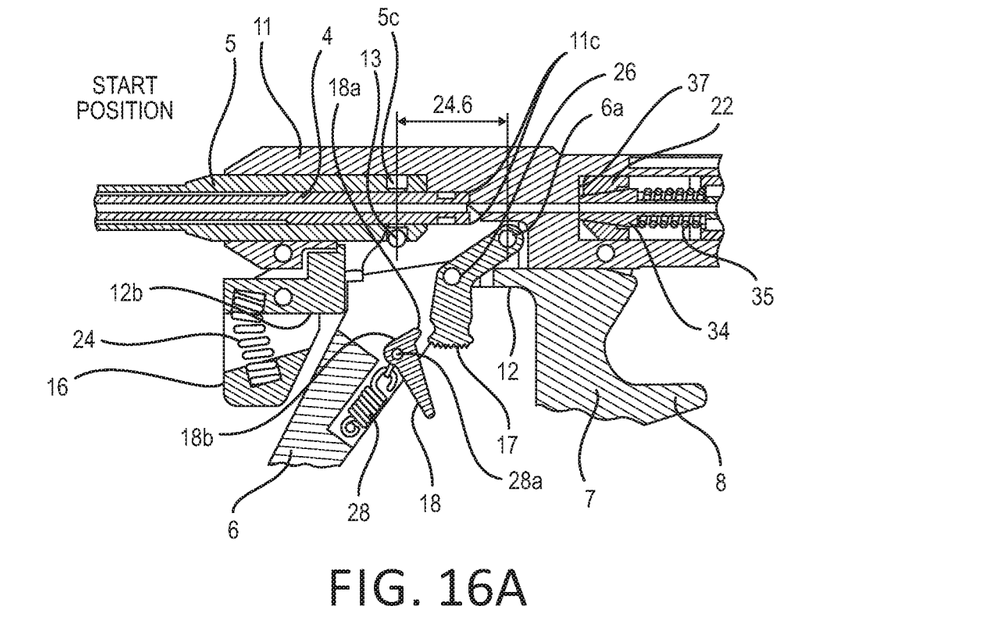
FIGS. 16A to 16D illustrate the motion of a ratchet assembly in the trigger-handle of FIG. 13 as the trigger is depressed.

FIG. 16A shows the ratchet and pawl assembly in a start position. Ratchet 17 is rotatably mounted to trigger 6 about hinge 26, and rotatably mounted to upper handle portion 12 by pin 6a. Pin 13 is mounted to trigger 6, and engages notch 5c in outer crimping tube. Pin 13 is slidably mounted in slot 12a, as shown in FIGS. 1 and 2. Outer crimping tube 5 surrounds inner crimping tube 4. Pawl 18 is rotatably mounted to trigger 6 by hinge 28a, and is biased by spring 28 into a rest position in which tooth 18*a* on pawl 18 is positioned near a toothed surface of ratchet 17. The proximal end of inner crimping tube 4 contacts a stopping surface 11*c* on the interior of housing 11, which may be seen in FIG. 13 in more detail.

Figure 16B:
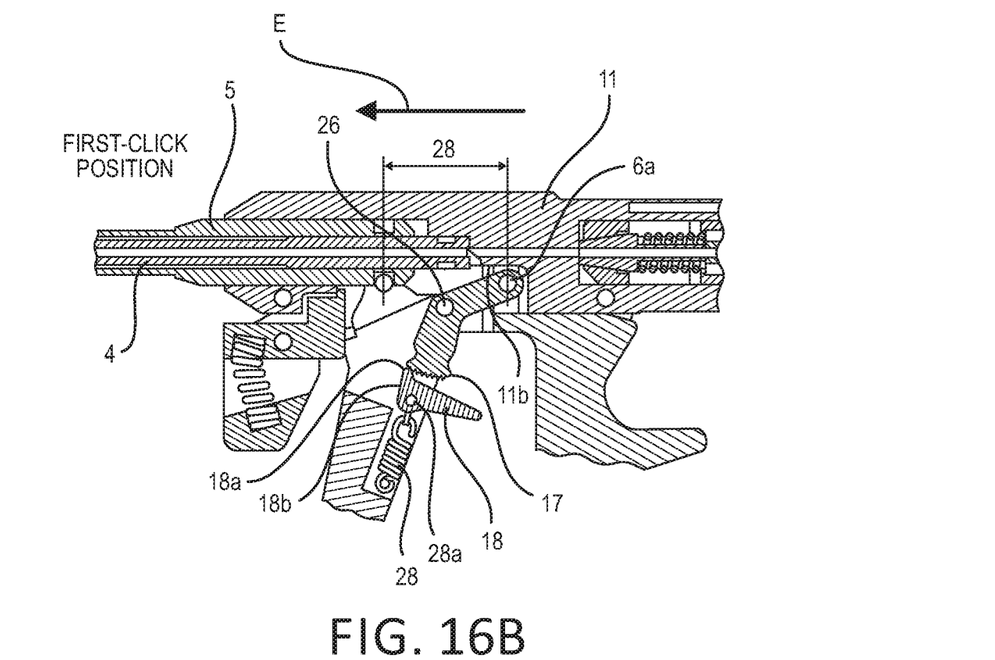

FIG. 16B shows the ratchet and pawl assembly in operation, as trigger 6 is squeezed toward palmrest 7. As the trigger moves toward the handle, the trigger rotates about hinge 26 on ratchet 18. Simultaneously, the portion of the ratchet connecting hinge 26 and pin 6*a* rotates toward the housing 11 about pin 6*a*. As the ratchet rotates toward housing 11, pin 13 moves distally relative to housing 11, driving outer crimping tube 5 in the direction of arrow E without moving inner crimping tube 4. As the trigger is squeezed toward the handle, tooth 18*a* on pawl 18 contacts the toothed surface of ratchet 17. This rotates the pawl about hinge 28*a* and applies tension to spring 28 by stretching the spring. When tooth 18*a* engages the teeth on the toothed surface of ratchet 17, the pawl can only pass the ratchet teeth in a single direction, toward handle 17. Thus, as long as tooth 18*a* engages ratchet 17, trigger 6 can only move in a forward direction toward the palmrest 7, and not in a reverse direction away from the handle. The portion of the ratchet connecting hinge 26 and pin 6*a* rotates toward the housing 11 until a desired angular rotation of the trigger 6 has been achieved, at which point the ratchet contacts a stopping surface 11*b* on housing 11. Before the desired angular rotation of the trigger 6 is achieved, the interaction between ratchet 17 and tooth 18*a* prevents motion of the trigger 6 away from palmrest 7. Should it become necessary to move trigger 6 away from palmrest 7, the pawl can be manually rotated about hinge 28*a* so that tooth 18*a* of pawl 18 disengages ratchet 17, allowing motion of the trigger 6 away from palmrest 7.

Figure 16C:
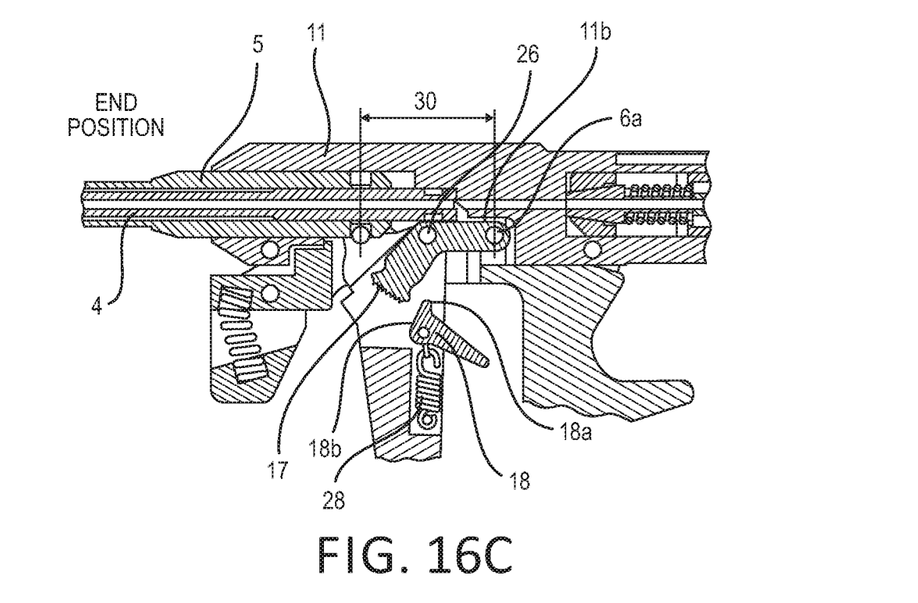

FIG. 16C shows the ratchet and pawl assembly after trigger operation. The portion of the ratchet connecting hinge 26 and pin 6*a* has contacted surface 11*b*, and therefore has achieved its maximum rotation toward the housing 11 about pin 6*a*. At this point, pin 13 has achieved its maximum distal motion relative to housing 11, and cannot drive outer crimping tube 5 any farther in a distal direction. At this point, tooth 18*a* no longer contacts the teeth of ratchet 17, and the pawl returns to its rest position under the biasing force of spring 28. At this point, the flat surface 18*b* of pawl 18 is in proximity to the teeth of ratchet 17.

Figure 16D:
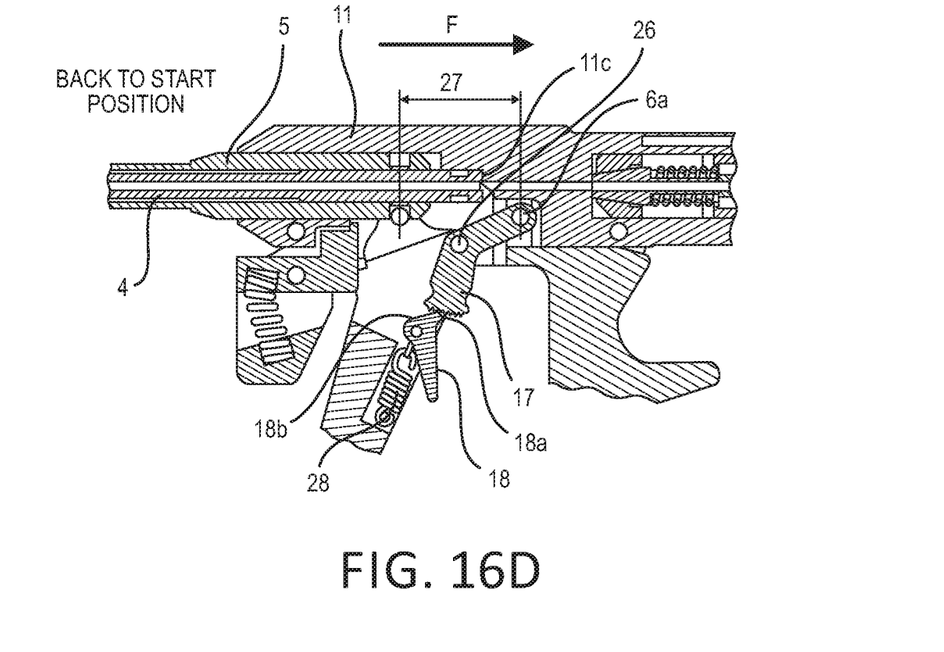

FIG. 16D shows the ratchet and pawl assembly returning to its initial start position. As shown in FIG. 16D, as the trigger returns to its initial position, the trigger rotates about hinge 26 and the ratchet rotates about pin 6*a*, the reverse of the motion shown in FIG. 16B. However, tooth 18*a* does not engage the teeth of ratchet 17. The planar surface 18*b* on pawl 18 engages the toothed surface of ratchet 17. Since the planar surface 18*b* is not configured to engage any teeth on ratchet 17, and does not fit between adjacent teeth on ratchet 17, planar surface 18*b* on pawl 18 moves freely past the teeth on ratchet 17, allowing the handle 6 to return to its initial start position as shown in FIG. 16A.

Figure 17:
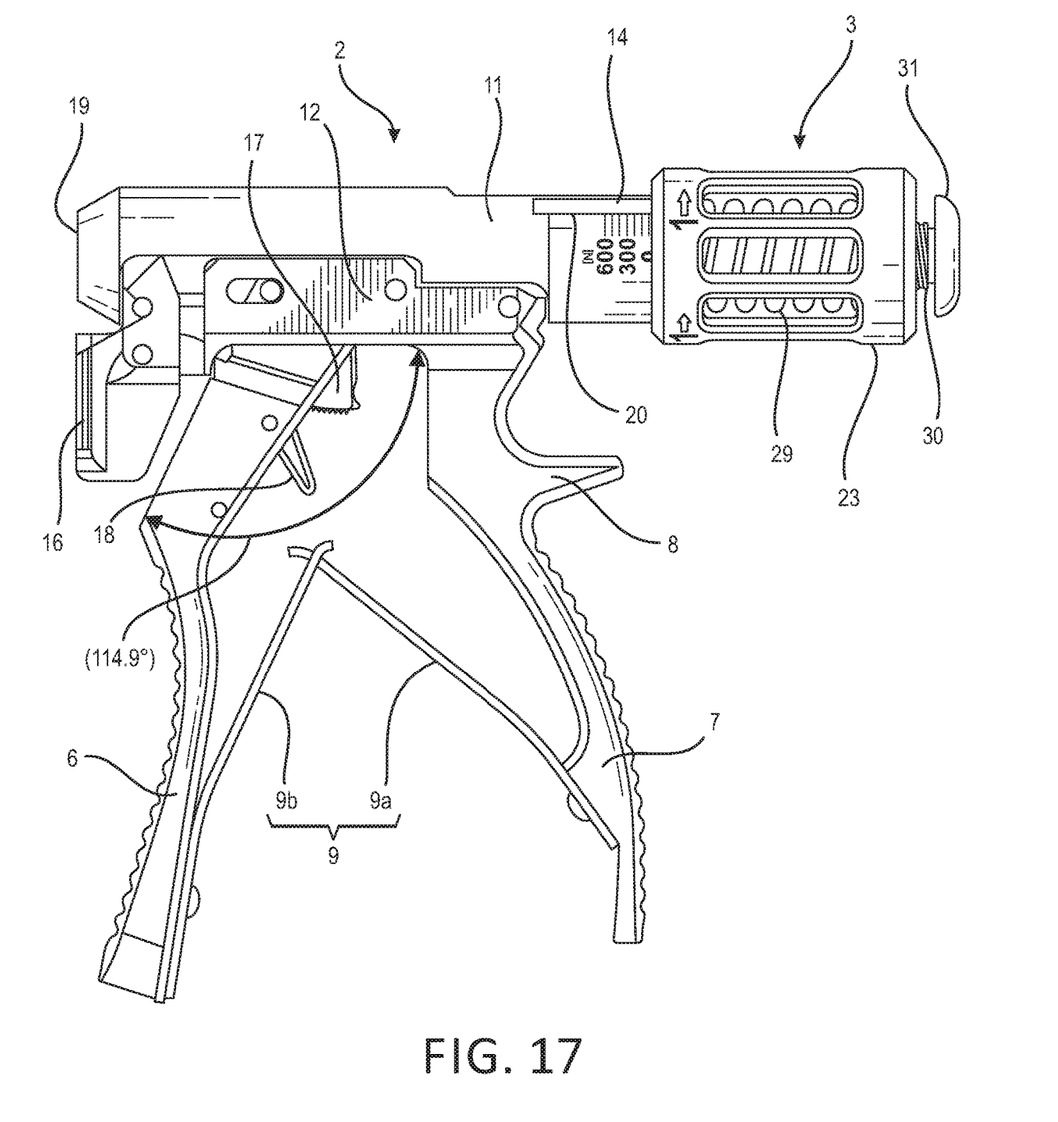
FIG. 17 is a side view of the trigger-handle unit of the crimping tool of FIG. 1, with a tensioning unit mounted thereto.

FIG. 17 shows the tensioning unit 3 connected with the trigger-handle unit 2, with the proximal end of housing 11 rotatably engaging rotatable tensioning nut 23. Leaf clip 14 engages a lip (not shown) inside nut 23. The cable passes through inner crimping tube 4 (not shown in FIG. 17) and housing 11, and then through tensioning unit 3. An outer spring 29 is visible in FIG. 17, positioned between the proximal end of the housing 11 and the proximal end of the tensioning nut 23. Tensioning rod 30 and end-stop nut 31 are shown at the proximal end of tensioning nut 23.

Figure 19:
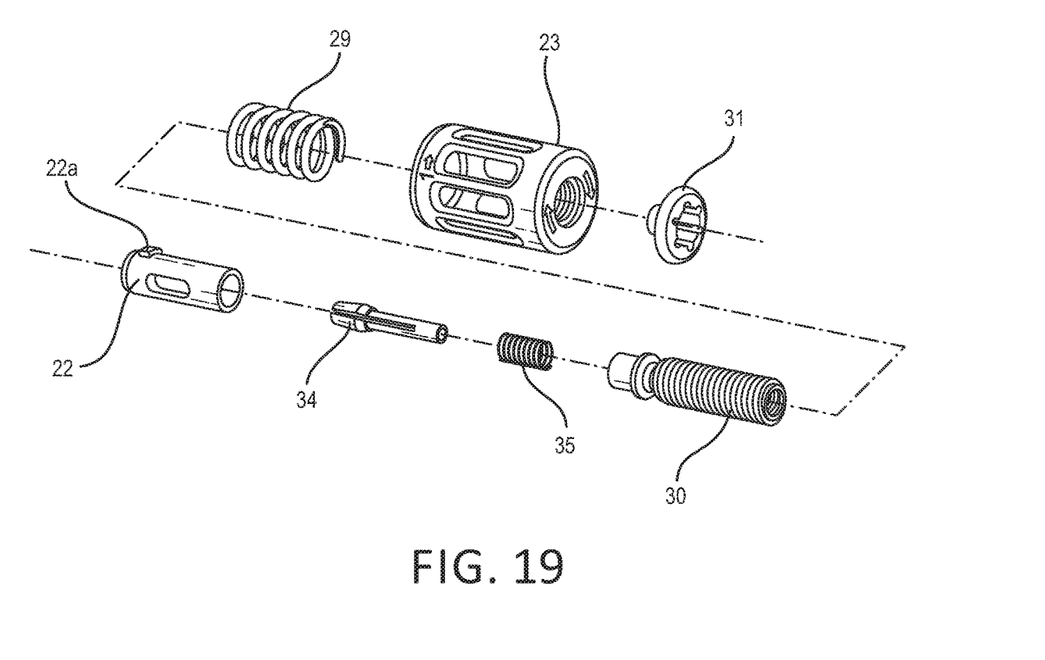
FIG. 19 is an exploded view of the tensioning unit.

FIG. 18 shows a detail of the assembled tensioning unit 3. The tensioning unit 3 may include a cone sheath 22, a collet 34 which is axially displaceable in the cone sheath 22, a guiding cam 22*a* which is connected to the cone sheath 22, a tensioning rod 30 which is connected to the cone sheath 22, a tensioning nut 23 which is rotatable on the tensioning rod 30, an inner spring 35 which is positioned between the collet 34 and the tensioning rod 30, an outer spring 29 which is positioned between the proximal end of the housing 11 and the tensioning nut 23, and an end-stop nut 31 which is mounted to the tensioning rod 30. An exploded view of these components is shown in FIG. 19. The cable to be tensioned is received in a bore 36 which extends from the distal end of collet 34, through tensioning rod 30 and end-stop nut 31.

The cable is passed through the center hole of the inner crimping tube 4 (not shown in FIG. 18), enters a proximal opening of collet 34, and exits through the tensioning rod 30 and the end-stop nut 31.

At rest, the tensioning nut 23 and end-stop nut 31 are in contact. The collet 34 contacts the surface 37 inside of the barrel of housing 11, and is displaced proximally relative to the cone sheath, thus opening the collet 34 for the cable to pass therethrough. This proximal displacement also compresses the inner spring 35.

Once the cable has been inserted through the collet, tension is applied by rotating tensioning nut 32 clockwise, compressing outer spring 29 and causing the inner assembly (end-stop nut 31, tensioning rod 30, cone sheath 22, and collet 34) to translate proximally without rotation. The collet 34 loses contact with surface 37 inside of the barrel of housing 11 due to the proximal translation, allowing the collet to contract radially and clamp the cable passing through bore 36.

Once tension has been applied, it is impossible to pull the cable towards the distal end of the handle-trigger unit 2 of FIG. 17 i.e., distally, because this pulls the collet 34 deeper into the cone sheath 22, increasing the clamping force on the cable 510. Pulling the cable towards a proximal end of the tensioning unit is still possible because this pulls the collet 34 out of the cone sheath 22 against inner spring 35, decreasing the clamping force on the cable.

As discussed above, the construction and operation of the tensioning unit are described in further detail in U.S. Pat. No. 9,956,021, incorporated for all purposes herein by reference.

The above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A crimping tool for crimping a cable, the crimping tool comprising:
   a crimping unit, including:
      an inner crimping tube having a distal end configured to receive the cable; and
      an outer crimping tube mounted around the inner crimping tube;
   a housing unit configured to receive the outer crimping tube, the housing unit comprising:
      a housing having an open lower portion;
      a trigger-handle;
      a first hinge connecting the trigger-handle to the housing; and
   a tensioning unit mounted to the housing, the tensioning unit being configured to apply tension to the cable;
   wherein:
      the trigger-handle is configured to releasably engage the open lower portion of the housing by rotation about the first hinge; and
      the outer crimping tube is configured to move in an axial direction relative to the inner crimping tube to crimp the cable when actuated by the trigger-handle.

2. The crimping tool of claim 1, wherein the trigger-handle is configured to releasably engage the open lower portion of the housing so as to hold the outer crimping tube between the housing and the trigger-handle.

3. The crimping tool of claim 1, wherein a groove on the outer crimping tube is configured to engage a pin on the trigger handle, said pin being configured to move the outer crimping tube over the distal end of the inner crimping tube when the trigger-handle is actuated.

4. The crimping tool of claim 3, wherein the distal end of the inner crimping tube is configured to radially contract when the outer crimping tube moves thereover.

5. The crimping tool of claim 1, wherein housing unit comprises a latching mechanism configured to releasably engage a pin on the housing.

6. The crimping tool of claim 1, wherein crimping is uniaxial without radial deflection of the cable.

7. The crimping tool of claim 1, wherein a groove on the outer crimping tube is configured to engage a pin on the trigger handle, and the proximal end of the inner crimping tube is configured to engage a stopping surface in the housing.

8. The crimping tool of claim 1, the inner crimping tube is made from a single part and the outer crimping tube is made from a single part.

9. The crimping tool of claim 1, wherein the trigger-handle comprises:
   an upper handle portion configured to engage the open lower portion of the housing by rotation about the first hinge;
   a palmrest connected with the upper handle portion; and
   a trigger connected to the upper handle portion by a second hinge,
   wherein the trigger is configured to:
      rotate about the second hinge in a single direction from a start position until a defined angular rotation has been achieved, and
      return to the start position after the defined angular rotation has been achieved.

10. The crimping tool of claim 1, wherein the trigger-handle comprises:
    an upper handle portion configured to engage the open lower portion of the housing by rotation about the first hinge;
    a palmrest connected with the upper handle portion; a trigger connected to the upper handle portion by a second hinge;
    a ratchet having a plurality of teeth connected with the upper handle portion; and
    a pawl connected with the trigger, said pawl having a first surface and a second surface,
    wherein the first surface of the pawl is configured to engage the plurality of teeth on the ratchet so as to allow rotation of the trigger about the second hinge in a single direction; and
    wherein the second surface of the pawl is configured to allow rotation of the trigger about the second hinge in a second direction opposite to the single direction.

11. The crimping tool of claim 10, wherein the second surface of the pawl does not engage the plurality of teeth on the ratchet, thereby allowing rotation of the trigger in the second direction.

12. The crimping tool of claim 1, wherein the trigger-handle comprises:
   an upper handle portion configured to engage the open lower portion of the housing by rotation about the first hinge;
   a palmrest connected with the upper handle portion; and
   a trigger connected to the upper handle portion by a second hinge;
   wherein the palmrest is an ergonomically designed palmrest.

13. The crimping tool of claim 12, wherein the ergonomically designed palmrest comprises:
   a rear surface configured to engage the palm of a user, and
   a horn spaced from the housing,
   wherein the horn is configured to engage the user's hand between a thumb and a forefinger.

14. The crimping tool of claim 12, wherein the trigger is an ergonomically designed trigger.

15. The crimping tool of claim 14, wherein the ergonomically designed trigger has an arc-shaped outer surface configured to engage the user's fingers.

16. A crimping tool for crimping a cable, the crimping tool comprising:
   a housing unit configured to receive an outer crimping tube and an inner crimping tube positioned in the outer crimping tube, the housing unit comprising:
      a housing having an open lower portion;
      a trigger-handle; and
      a first hinge connecting the trigger-handle to the housing; and
   a tensioning unit mounted to the housing, the tensioning unit being configured to apply tension to a cable in the inner crimping tube;
   wherein:
      the trigger-handle is configured to releasably engage the open lower portion of the housing by rotation about the first hinge; and
      the trigger-handle is configured to drive the outer crimping tube in a distal direction relative to the inner crimping tube to crimp the cable.

* * * * *